US011959921B2

United States Patent
Yu et al.

(10) Patent No.: US 11,959,921 B2
(45) Date of Patent: Apr. 16, 2024

(54) DENDRITIC MESOPOROUS SILICA NANOPARTICLES SYNTHESIZED VIA A FACILE ONE-POT SURFACTANT-FREE PROCESS

(71) Applicant: THE UNIVERSITY OF QUEENSLAND, St Lucia (AU)

(72) Inventors: Chengzhong (Michael) Yu, Sinnamon Park (AU); Jianye Fu, St Lucia (AU); Jinqing Jiao, Beijing (CN); Yang Liu, Woolloongabba (AU)

(73) Assignee: THE UNIVERSITY OF QUEENSLAND, St. Lucia (AU)

( * ) Notice: Subject to any disclaimer, the term of this patent is extended or adjusted under 35 U.S.C. 154(b) by 603 days.

(21) Appl. No.: 16/621,548

(22) PCT Filed: Jun. 12, 2018

(86) PCT No.: PCT/AU2018/050579
§ 371 (c)(1),
(2) Date: Dec. 11, 2019

(87) PCT Pub. No.: WO2018/227240
PCT Pub. Date: Dec. 20, 2018

(65) Prior Publication Data
US 2021/0292177 A1    Sep. 23, 2021

(30) Foreign Application Priority Data

Jun. 12, 2017    (WO) ................ PCT/AU2017/050584

(51) Int. Cl.
*C01B 33/18*    (2006.01)
*C01B 32/15*    (2017.01)
(Continued)

(52) U.S. Cl.
CPC .......... *G01N 33/588* (2013.01); *C01B 32/15* (2017.08); *C01B 33/113* (2013.01); *C01B 33/18* (2013.01);
(Continued)

(58) Field of Classification Search
None
See application file for complete search history.

(56) References Cited

U.S. PATENT DOCUMENTS

2004/0101822 A1    5/2004    Wiesner et al.
2015/0031575 A1    1/2015    Fu et al.

FOREIGN PATENT DOCUMENTS

WO    2016/164987    10/2016

OTHER PUBLICATIONS

Liu et al., Kinetically controlled assembly of nitrogen-doped invaginated carbon nanospheres with tunable mesopores, Mesoporous Materials, Sep. 2016, 22, 14962-14967 (Year: 2016).*

(Continued)

*Primary Examiner* — Coris Fung
*Assistant Examiner* — Keling Zhang
(74) *Attorney, Agent, or Firm* — Nixon & Vanderhye P.C.

(57) ABSTRACT

A method for forming dendritic mesoporous nanoparticles comprising preparing a mixture containing one or more polymer precursors, a silica precursor, and a compound that reacts with silica and reacts with the polymer or oligomer formed from the one or more polymer precursors, and stirring the mixture whereby nanoparticles are formed, and subsequently treating the nanoparticles to form dendritic mesoporous silica nanoparticles or dendritic mesoporous carbon nanoparticles. The silica precursor may comprise tetraethyl orthosilicate (TEOS), the one or more polymer precursors may comprise 3-aminophenol and formaldehyde and the compound may be ethylene diamine (EDA). There (Continued)

is a window of amount of EDA present that will result in asymmetric particles being formed. If a greater amount of EDA is present, symmetrical particles will be formed.

17 Claims, 8 Drawing Sheets

(51) Int. Cl.
  C01B 33/113      (2006.01)
  C01B 37/02       (2006.01)
  G01N 21/64       (2006.01)
  G01N 33/543      (2006.01)
  G01N 33/58       (2006.01)
  B82Y 15/00       (2011.01)
  B82Y 30/00       (2011.01)
  B82Y 40/00       (2011.01)

(52) U.S. Cl.
  CPC ............ *C01B 33/185* (2013.01); *C01B 37/02* (2013.01); *G01N 21/64* (2013.01); *G01N 33/54346* (2013.01); *G01N 33/587* (2013.01); *B82Y 15/00* (2013.01); *B82Y 30/00* (2013.01); *B82Y 40/00* (2013.01); *C01P 2004/62* (2013.01); *C12Y 111/01007* (2013.01)

(56) References Cited

OTHER PUBLICATIONS

Pramila Ghimire, et al., "Tetraethyl ortosilicate-assisted synthesis of nitrogen-containing porous carbon spheres", Carbon, vol. 121, Jun. 2, 2017, pp. 408-417.
Karin Möller, et al., "Highly efficient siRNA delivery from core-shell mesoporous silica nanoparticles with multifunctional polymer caps", Nanoscale, vol. 8, No. 7, 2016, pp. 4007-4019.
Doo-Sik Moon, et al., "Tunable Synthesis of Hierarchical Mesoporous Silica Nanoparticles with Radial Wrinkle Structure", Langmuir, vol. 28, No. 33, published Aug. 3, 2012, pp. 12341-12347.
Dechao Niu, et al., "Synthesis of Core-Shell Structured Dual-Mesoporous Silica Spheres with Tunable Pore Size and Controllable Shell Thickness", Journal of the American Chemical Society, vol. 132, No. 43, pp. 15144-15147.
Jing-Chuan Song, et al., "Controllable synthesis of hollow mesoporous silica particles by a facile one-pot sol-gel method", Chemical Communications, vol. 51, No. 52, pp. 10517-10520.
Jin-Gui Wang, et al., "Anionic surfactant-templated mesoporous silica (AMS) nano-spheres with radially oriented mesopores", Journal of Colloid and Interface Science, vol. 323, No. 2, pp. 332-337.
Chun Xu, et al., "Core-Cone Structured Monodispersed Mesoporous Silica Nanoparticles with Ultra-large Cavity for Protein Delivery", Small, vol. 11, No. 44, 2015, pp. 5949-5955.
International Search Report for PCT/AU2018/050579 dated Aug. 28, 2018, 4 pages.
Written Opinion of the ISA for PCT/AU2018/050579 dated Aug. 28, 2018, 10 pages.
Li, Dong, et al., "One-pot synthesis of surface roughness controlled hollow silica spheres with enhanced drug loading and release profiles under ambient conditions in aqueous solutions," Journal of Materials Chemistry B, vol. 1, No. 40, 2013, pp. 5515-5520, XP055514945.
Liu, Hui, et al., "Preparation of Porous Hollow SiO2 Spheres by a Modified Stober Process Using MF Microspheres as Templates," Journal of Cluster Science, vol. 23, No. 2, Dec. 6, 2011, pp. 273-285, XP035058320.
Song, Jing-Chuan, et al., "Supplementary Information Controllable Synthesis of Hollow Mesoporous Silica Particles by a Facile One-Pot Sol-Gel Method," Nov. 25, 2015, http://www.rsc.org/suppdata/c5/cc/c5cc03025k/c5cc03025k1.pdf retrieved Dec. 22, 2020, 7 pages, XP055762320.
Extended European Search Report dated Jan. 15, 2021, issued in European Application No. 18817021.1, 10 pages.
Bogush, G. H., et al., "Uniform Silica Particle Precipitation: An Aggregative Growth Model", Journal of Colloid and Interface Science, vol. 142, No. 1, Mar. 1, 1991, pp. 19-34.
Fuertes, Antonio B., et al., "One-step synthesis of silica@resorcinol-formaldehyde spheres and their application for the fabrication of polymer and carbon capsules", Chemical Communications, vol. 48, 2012, pp. 6124-6126.
Han, Mingyong, et al., "Quantum-dot-tagged microbeads for multiplexed optical coding of biomolecules", Nature Biotechnology, vol. 19, No. 7, Jul. 2001, pp. 631-635.
Knežević, Nikola Ž., et al., "Magnetic mesoporous silica-based core/shell nanoparticles for biomedical applications", RSC Advances, vol. 3, No. 25, 2013, pp. 9584-9593.
Sanz-Ortiz, Marta N., et al., "Templated Growth of Surface Enhanced Raman Scattering-Active Branched Gold Nanopoarticles within Radial Mesoporous Silica Shells", ACS Nano, vol. 9, No. 10, 2015, pp. 10489-10497.
Slowing, Igor I., et al., "Mesoporous Silica Nanoparticles for Drug Delivery and Biosensing Applications, Advanced Functional Materials", vol. 17, No. 8, 2007, pp. 1225-1236.
Wang, Wenxing, et al., "Facile Synthesis of Uniform Virus-like Mesoporous Silica Nanoparticles for Enhanced Cellular Internalization", ACS Central Science, vol. 3, 2017, pp. 839-846.
Yang, Peipei, et al., "Encapsulated Silver Nanoparticles Can Be Directly Converted to Silver Nanoshell in the Gas Phase", Nano Letters, vol. 15, 2015, pp. 8397-8401.

* cited by examiner

DENDRITIC MESOPOROUS SILICA NANOPARTICLES SYNTHESIZED VIA A FACILE ONE-POT SURFACTANT-FREE PROCESS

This application is the U.S. national phase of International Application No. PCT/AU2018/050579 filed Jun. 12, 2018 which designated the U.S. and claims priority to International Patent Application No. PCT/AU2017/050584 filed Jun. 12, 2017, the entire contents of each of which are hereby incorporated by reference.

TECHNICAL FIELD

The present invention relates to a method for forming mesoporous nanoparticles. The mesoporous nanoparticles may be symmetric or asymmetric particles. The mesoporous nanoparticles may comprise dendritic mesoporous nanoparticles. The present invention also relates to generally symmetric mesoporous nanoparticles. The nanoparticles may be carbon nanoparticles or silica nanoparticles.

BACKGROUND ART

Nanoparticles are generally considered to comprise particles having a maximum particle size that is less than 1 mm. Nanoparticles are attracting widespread interest in both the research community and in industry for their role as possible delivery agents for feedstuffs and nutritional products, insecticides, pesticides, therapeutic agents and vaccines. Further, nanoparticles can also be used for carrying biochemical markers, tags or labels that can be used in immunoassays or other detection methods. For example, our international patent application number PCT/AU2017/050584 describes methods and kits for detecting an analyte by contacting the analyte with a nanoparticle, such as a silica nanoparticle.

Dendritic mesoporous silica nanoparticles combine the structural characteristics and mechanical strength of organic dendritic molecules, as well as the large specific surface area and pore volume, which has led to a wide range of research interests. In addition, the dendritic branches stretch from the centre of the nanoparticles outwards, providing an entirely continuous porous space that is different from conventional nanoporous materials where the nanopores are isolated to some extent.

Hybrid multicompartment colloidal nanomaterials have attracted significant research interest both in material synthesis methods and their wide variety of applications.[1,2] Multicompartment nanoparticles integrate different subdomains into one nanoparticle which possess properties that are not found in single component systems.[3]

Among all the hybrid multicomponent colloidal nanoparticles, heterotrimer, which refer to those with three different nanoparticulate components in intimate contact in one nanoparticle are attracting research attention.[4,5] To tailor the structure and control the properties of heterotrimeric nanoparticles, during the past few years, a wide variety of techniques have been proposed,[6] such as, emulsion polymerization,[7] partial surface modification,[8,9] microfluidics,[10,11,10] and templated-based self-assembly.[11,12] General growth mechanisms proposed for the formation of nanosized hybrid multicomponent colloidal nanoparticles are direct heterogeneous nucleation, reaction at liquid-liquid interface and thermal induced attachment of preformed heteroparticles.[11] Under all mechanisms, all previous reports involving the synthesis of heterotrimeric nanoparticles can only be achieved by sequential growth of the other compartments on preformed seed particles through a three-step seed-mediated approaches.[7,13-21] There are no reports on synthesis heterotrimeric nanoparticles via a one-pot and surfactant-free method.[21]

Moreover, to successfully assemble hetrotrimeric nanoparticles, distinct surface chemistry differences are usually required for the combination of different materials,[22] The design and fine control of heterotrimeric nanoparticles through bottom-up approaches between materials with similar properties still remains a major challenge.[4,23,24]

Nowadays, many type of nanoparticles have been introduced in biological applications such as gene transfection,[27] intracellular drug delivery[28] and imaging,[29] which require the cellular uptake of the nanomaterials into the cell membrane.[30] As is well known, the type of a cell line plays a key role in the endocytic process of nanoparticles, which resulted in various cellular uptake pathways.[31,32] Cells can uptake nanoparticles through several endocytic pathways, such as phagocytosis, micropinocytosis, caveolae-mediated endocytosis, clathrin- and caveolae-independent endocytosis.[33] Since most cells have some phagocytic capacity,[34], cells can be divided into three groups based on the phagocytic capacity of a cell, professional phagocytes, non-professional phagocytes.[35] As is widely accepted that, for a professional phagocyte, i.e., macrophages, phagocytosis is the main efficient endocytic pathway to uptake nanoparticle.[34,36] For non-professional phagocytes, a set of fibroblasts or epithelial cells are capable of phagocytosis. For example, the intestinal or colonic epithelial cells have intermediate phagocytic capacity.[37-39] While some epithelial cells possess low phagocytic capacity.[34] Besides the influence of the cell type on the endocytic capacity, the morphology of nanoparticles also matters. Previous researches have shown that the shape,[40-42] aspect ratio[43-45] and orientation[46,47] of nanoparticles can greatly influence the cellular uptake, and most of which show cell type dependent behaviour.[48] Several recent reports have also demonstrated that nanoparticles with spikes on the surface forming virus-like structure or rough surface show good cellular uptake property[49] or enhanced adhesion toward bacteria membrane.[50] However, whether the symmetry of the virus-like or rough surface nanoparticles influence the cellular uptake is not clear. It is significant and urgent to understand the cellular uptake behaviours of nanoparticles with opposite symmetries.

It will be clearly understood that, if a prior art publication is referred to herein, this reference does not constitute an admission that the publication forms part of the common general knowledge in the art in Australia or in any other country.

SUMMARY OF INVENTION

The present invention is directed to a method for forming dendritic mesoporous nanoparticles, which may at least partially overcome at least one of the abovementioned disadvantages or provide the consumer with a useful or commercial choice.

With the foregoing in view, the present invention in one form, resides broadly in a method for forming dendritic mesoporous nanoparticles comprising preparing a mixture containing one or more polymer precursors, a silica precursor, and a compound that reacts with silica and reacts with the polymer or oligomer formed from the one or more polymer precursors, and stirring the mixture whereby nanoparticles are formed, and subsequently treating the nanoparticles to form dendritic mesoporous silica nanoparticles or dendritic mesoporous carbon nanoparticles.

Advantageously, the present invention allows for the formation of dendritic mesoporous nanoparticles without requiring use of a surfactant. Previous attempts to produce dendritic mesoporous nanoparticles frequently used surfactants. As a further advantage, the process of the present invention may be conducted in a single pot, thereby enabling simple synthesis. Embodiments of the invention do not add any seed particles to the reaction mixture.

In one embodiment of the present invention, the compound that reacts with silica and reacts with the polymer or oligomer formed from the one or more polymer precursors enhances interaction between the primary silica particles and the polymer or oligomers formed from the one or more polymer precursors. In one embodiment, the compound that reacts with silica and reacts with the polymer or oligomer formed from the one or more polymer precursors acts as a binder to facilitate deposition of a polymer or oligomer formed from the one or more polymer precursors on the primary silica particles. In one embodiment, the compound that reacts with silica and reacts with the polymer or oligomer formed from the one or more polymer precursors reacts with the silica precursor or reacts with silicate formed from the silica precursor, or facilitates reaction between the silica precursor or silicate formed from the silica precursor and the one or more polymer precursors or polymers or oligomers formed from the one or more polymer precursors.

In one embodiment, the silica precursor comprises a silica precursor that reacts more quickly than the one or more polymer precursors such that a primary silica particle is initially formed, followed by formation of further silica and polymer or oligomers that are laid down on the primary silica particles. This results in the formation of particles that comprise the primary silica particles having extra silica and polymer growing from the surface thereof. Once the reactants have been consumed or the particles removed from the reaction mixture, the particles may be treated to either remove the carbon-containing components or remove the silica containing components to form dendritic silica mesoporous nanoparticles or dendritic carbon mesoporous nanoparticles, respectively.

In one embodiment, the one or more polymer precursors start to form polymers or oligomers after nucleation of silica has started. In one embodiment, the one or more polymer precursors must overcome an energy barrier for nucleation before polymers or oligomers start to form.

In one embodiment, the compound that reacts with silica and reacts with the polymer or oligomer formed from the one or more polymer precursors is present in an amount such that heterogeneous nucleation of polymer and silica on the primary silica particles is promoted. In this embodiment, symmetrical nanoparticles can be obtained.

In another embodiment, the compound that reacts with silica and reacts with the polymer or oligomer formed from the one or more polymer precursors is present in an amount such that formation of a region of polymer or oligomer on a surface of the primary silica particles is formed, with further polymer or oligomer growing on the region of polymer or oligomer whilst further silica grows on the remaining surface of the primary silica particles, followed by the silica precursor reacting with oligomers polymers formed from the one or more polymeric precursors whereby oligomers containing silicate and the one or more polymer precursors or oligomers thereof deposit on the silica surface of the primary particles. In this embodiment, asymmetric nanoparticles can be formed.

In one embodiment, the compound that reacts with silica and reacts with the polymer or oligomer formed from the one or more polymer precursors is a positively charged compound or has a net positive surface charge.

In one embodiment, the compound that reacts with silica and reacts with the polymer or oligomer formed from the one or more polymer precursors comprises an organic amine, such as alkyl, alkene, alkyne or aryl amine, or an alkyl, alkene, alkyne or aryl diamine, or an alkyl, alkene, alkyne or aryl triamine. In one embodiment, the compound that reacts with silica and reacts with the polymer or oligomer formed from the one or more polymer precursors comprises ethylenediamine. The present inventors expect that any compound that could convert the negatively charged silica surface to a positively charged surface and then bind to the polymer/oligomer matrix would work satisfactorily. Another example is cetyltrimethylammonium bromide, which is a quaternary ammonium surfactant.

In one embodiment, the polymer that is formed is negatively charged or has a net negative surface charge and the compound that reacts with silica and reacts with the polymer or oligomer formed from the one or more polymer precursors has a positive charge or a net positive surface charge. Depending upon the amount of compound present, it will be possible to obtain either asymmetric nanoparticles or symmetric nanoparticles. In this regard, the amount of the compound used in the reaction can tune the interaction between silica and polymer and result in various structures.

If the amount of compound is in the range suitable for forming asymmetric particles, it is believed that the reaction mechanism involves initial formation of the primary silica particles. The positively charged compound functions as a binder, which can react with both the primary silica particles and the polymer or oligomer that is also being formed. Consequently, oligomer can start to grow on part of the surface of the primary silica particle. Once oligomer has started to deposit onto the primary silica particles surface, further oligomer preferentially deposits on that surface. At the same time, silica continues to be deposited on the surface of the primary silica particles. As a result, the primary silica particles now have a region of oligomer/polymer on part of the surface of the primary silica particles and a region of silica on part of the surface. When the formation rate of silica decreases due to depletion of the silica precursor in the reaction mixture, there will only be a limited amount of silicate oligomers present in the reaction mixture. The compound facilitates reaction of the silicate oligomers with the oligomers of polymer present in the mixture, with the silica/polymer oligomers preferentially depositing on the silica surface of the particles and the polymer oligomers preferentially depositing on the polymer on the silica particles. As a result, the particles have a surface region that is rich in the polymer oligomers and a surface region that is rich in silica and/or silicate/polymer oligomers. When the particles are treated to form either silica nanoparticles or carbon nanoparticles, asymmetric particles are formed. The nanoparticles may have an "acorn" morphology.

If the amount of compound is in the range suitable for forming symmetric particles, it is believed that the reaction mechanism is influenced by the compound consuming or reacting with a polymer precursor and promoting heterogeneous nucleation of silica and polymer relatively evenly over the surface of the primary silica particles. This results in the formation of symmetrical particles. When either the silica or carbon-containing components are subsequently removed, symmetric dendritic nanoparticles are obtained.

In general terms, a greater amount of the compound is required to form symmetrical particles and a lesser amount of the compound is required to form the asymmetric particles. It is believed that there will be a window of operation where the amount of the compound in the reaction mixture will result in the formation of asymmetric nanoparticles. If a greater amount of the compound is present in the reaction mixture, symmetric particles will be formed. If the compound is not present or is present below a minimum value, it is believed that separate particles of silica will be formed and separate particles of polymer will be formed.

In one embodiment, the one or more polymer precursors comprise resorcinol-formaldehyde, aminophenol-formaldehyde or dopamine. The silica precursor may comprise tetraethyl orthosilicate (TEOS), tetrapropyl orthosilicate (TPOS) or tetrabutoxysilane (TBOS), tetramethyl orthosilicate (TMOS) or other silica precursors known to those skilled in the art. Under the reaction conditions used, the silica precursor may form silica. Alternatively, the silica precursor may form a silicon containing material that may be subsequently converted to silica.

In one embodiment, the reaction mixture further comprises an alcohol and water. The alcohol may be ethanol.

The reaction mixture may include an alkali material. The alkali material may comprise ammonia. The reaction may occur at an alkaline or basic pH. The reaction may take place at a pH in the range of from about 8 to 11.

In one embodiment, the compound comprises ethylenediamine (EDA) and the one or more polymer precursors comprise 3-aminophenol and formaldehyde. The mass ratio of EDA to (3-aminophenol and formaldehyde) may fall within a range of from 0.20 to 0.28, or from 0.23 to 0.27, in order to form asymmetric particles. It is believed that if the mass ratio of EDA to (3-aminophenol and formaldehyde) is greater than 0.28 or greater than 0.29, symmetrical particles will be formed. If the mass ratio of EDA to (3-aminophenol and formaldehyde) is less then 0.20, it is believed that separate particles of silica and separate particles of polymer are likely to be formed.

In some embodiments, the molar ratio of EDA to TEOS may fall within a range of from 0.20 to 0.46, in order to form asymmetric particles. It is believed that if the molar ratio of EDA to TEOS is greater than 0.46, symmetrical particles will be formed. If the molar ratio of EDA to (3-aminophenol and formaldehyde) is less then 0.20, it is believed that separate particles of silica and separate particles of polymer are likely to be formed.

The reaction may take place at temperatures in the range of from 0° to 75° C. The present inventors have found that temperature influences the particle size, with higher temperatures resulting in small particle sizes.

Once the reaction is complete, the particles comprise heterotrimeric particles having regions of silica, regions of polymer and regions of silicate/polymer oligomers.

Once the reaction is complete, the particles may be removed or separated from the liquid phase by any suitable method, such as centrifuge or by passing through hydrocyclones. The particles may then be washed and dried and then treated to form either silica nanoparticles or carbon nanoparticles.

In order to form silica nanoparticles, the particles are preferably calcined in air or an oxygen containing atmosphere to thereby burn out the polymer, leaving behind the silica nanoparticles. Calcination may take place at any appropriate temperature, such as a temperature of from 500° to 1000° C., or from 500° to 700° C.

In order to form carbon nanoparticles, the particles are suitably carbonised by heating in an inert or reducing atmosphere or in an atmosphere that is essentially free of oxygen to carbonise the polymer, followed by selective leaching/etching of the silica from the particles. Selective leaching/etching of the silicon from the particles may be achieved using hydrofluoric acid.

In embodiments where asymmetric nanoparticles are formed, the particles may have a maximum particle size of up to 1000 nm, or up to 900 nm, or up to 800 nm. The particles may have a minimum particle size of 100 nm, or 150 nm, or 200 nm.

In a second aspect, the present invention provides a method for forming dendritic mesoporous nanoparticles comprising preparing a mixture containing one or more polymer precursors, a silica precursor, and a compound that enhances interaction between the primary silica particles and the polymer or oligomers formed from the one or more polymer precursors, and stirring the mixture whereby nanoparticles are formed, and subsequently treating the nanoparticles to form dendritic mesoporous silica nanoparticles or dendritic mesoporous carbon nanoparticles.

In a third aspect, the present invention provides a method for forming dendritic mesoporous nanoparticles comprising preparing a mixture containing one or more polymer precursors, a silica precursor, and a compound that acts as a binder to facilitate deposition of a polymer or oligomer formed from the one or more polymer precursors on the primary silica particles, and stirring the mixture whereby nanoparticles are formed, and subsequently treating the nanoparticles to form dendritic mesoporous silica nanoparticles or dendritic mesoporous carbon nanoparticles.

In a fourth aspect, the present invention provides a method for forming dendritic mesoporous nanoparticles comprising preparing a mixture containing one or more polymer precursors, a silica precursor, and a compound that reacts with the silica precursor or reacts with silicate formed from the silica precursor, or facilitates reaction between the silica precursor or silicate formed from the silica precursor and the one or more polymer precursors or polymers or oligomers formed from the one or more polymer precursors, and stirring the mixture whereby nanoparticles are formed, and subsequently treating the nanoparticles to form dendritic mesoporous silica nanoparticles or dendritic mesoporous carbon nanoparticles.

Embodiments of the second, third and fourth aspects of the present invention may utilise the same features as described for embodiments of the first aspect of the present invention. For convenience and brevity, description of these embodiments will not be repeated.

In a fifth aspect, the present invention provides symmetrical silica nanoparticles comprising a solid core having outgrowths of silica extending from the solid core.

The symmetrical silica nanoparticles may have a pore size between 7 to 20 nm. The pore size may be defined by the space between the outgrowths of silica extending from the solid core.

In a sixth aspect, the present invention provides symmetrical carbon nanoparticles comprising a hollow core having outgrowths of carbon extending from the hollow core. The hollow core may be mesoporous.

The method of preferred embodiments of the present invention can produce dendritic mesoporous nanoparticles using a one pot synthesis technique that does not require surfactants. The method is scalable and produces good yield of nanoparticles. The method may be controlled to produce symmetrical nanoparticles or asymmetric nanoparticles.

Silica nanoparticles may be formed or carbon nanoparticles may be formed. It is not necessary to add seed particles to the reaction mixture.

Any of the features described herein can be combined in any combination with any one or more of the other features described herein within the scope of the invention.

The reference to any prior art in this specification is not, and should not be taken as an acknowledgement or any form of suggestion that the prior art forms part of the common general knowledge.

BRIEF DESCRIPTION OF DRAWINGS

Various embodiments of the invention will be described with reference to the following drawings, in which.

DESCRIPTION OF EMBODIMENTS

Example 1—Preparation of Symmetric Particles

Figure 1:
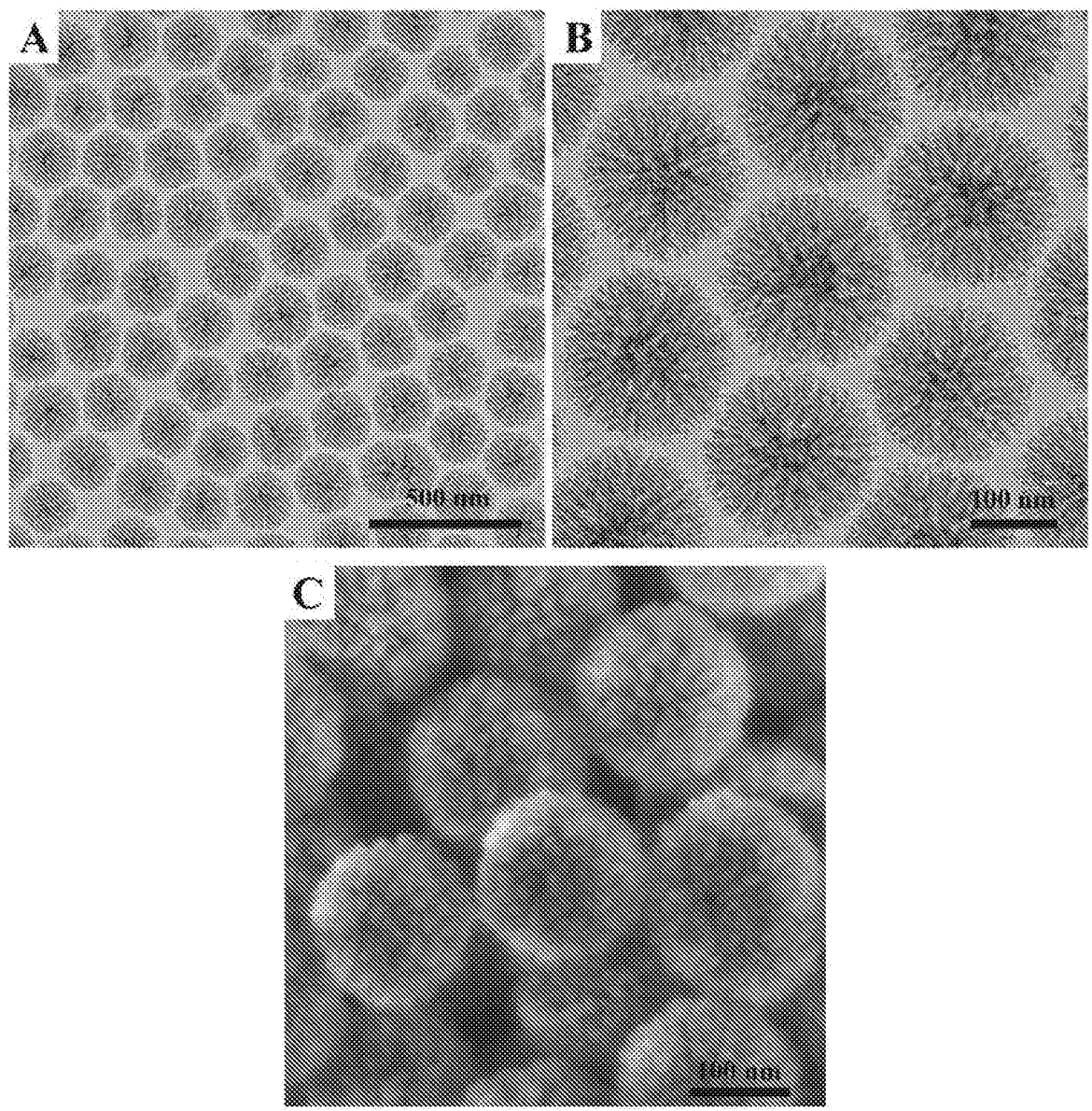
FIG. 1 shows (A) and (B) TEM images and (C) SEM image of the monodisperse mesa porous silicon nanoparticles of example 1.

Monodisperse mesoporous silica nanoparticles were synthesized via a facile one-pot, surfactant-free process under the well-known Stöber synthesis condition. Typically, an aqueous-alcoholic solution was prepared by mixing ethanol (40 mL), distilled water (10 mL), ammonium hydroxide (1.56 mL) and ethylenediamine solution (EDA, 0.225 mL) under stirring at 60° C. After that, 3-aminophenol (0.412 g), formaldehyde solution (0.9 mL), TEOS (1.56 mL) were added to the above-mentioned solution. Then the mixture was vigorously stirred for 5 h. The as synthesized composite was collected by centrifugation, ethanol washing and drying. Finally, monodisperse mesoporous silica nanoparticles were harvested after calcination in air, noted as DMSN-M.

TEM images (FIG. 1A) showed that the well dispersed silicon nanoparticles with a uniform morphology are obtained. As shown in FIG. 1B, the mean particle diameter is approximately 180+ or −5 nm in the particles exhibit nano-sized radial spikes. An SEM image (FIG. 1C) further shows the uniform size silicon nanoparticles with a dense distribution of silica spikes. The nitrogen adsorption and desorption isotherm (FIG. 2) shows a typical type IV isotherm with distinct hysteresis loops, which indicates the existence of a high degree of miso porosity. The corresponding Barrett-Joyner-Halenda (BJH) pore size distribution curve (FIG. 2, the insert curve, derived from the adsorption breads exhibits a relatively broad peak centred at 9.1 nm.

Figure 3:
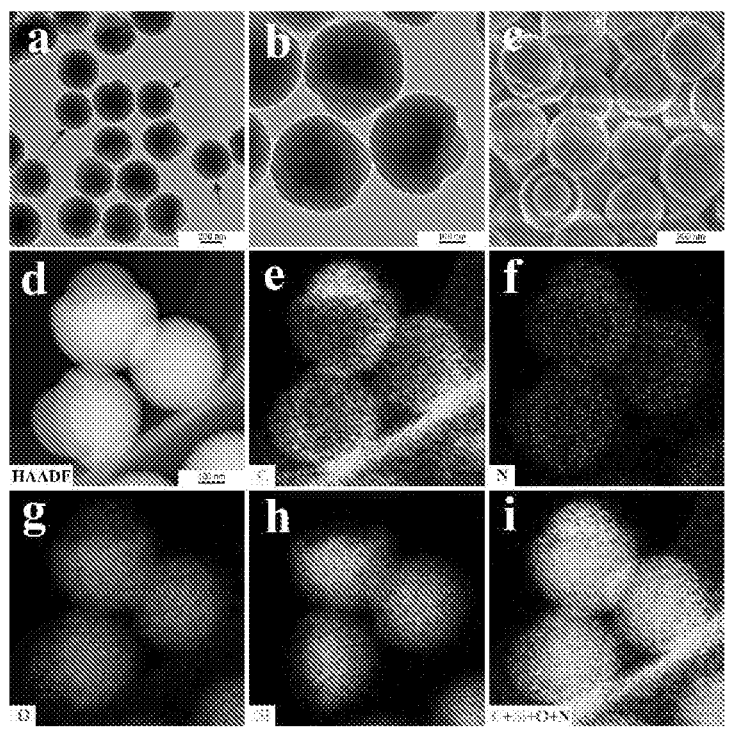
FIG. 3 shows TEM, SEM and STEM EDS mapping images of the prepared ABC heterotrimeric nanoparticles. (a, b) TEM images; (c) SEM image; (d) HAADF-STEM image; (e-i) EDX elemental mapping of C, N, O, Si and colour overlays, respectively, of the nanoparticles obtained in example 2.
Figure 4:
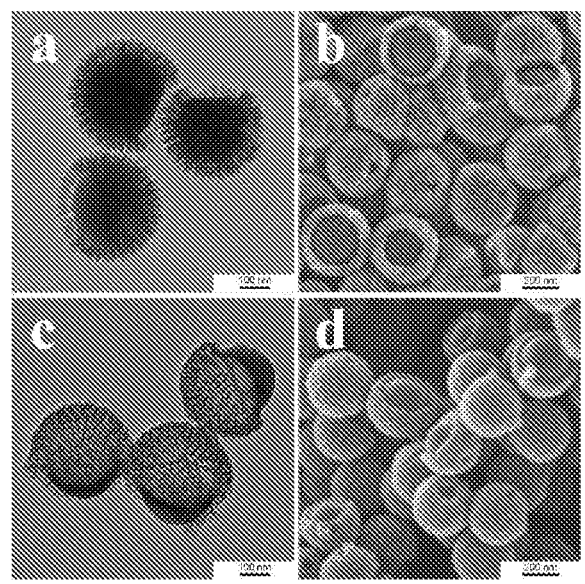
FIG. 4 shows TEM (a, c) and SEM (b, d) images of the asymmetric nanoparticles. (a, b) asymmetric silica nanoparticles, (c, d) asymmetric carbon nanoparticles.
Figure 5:
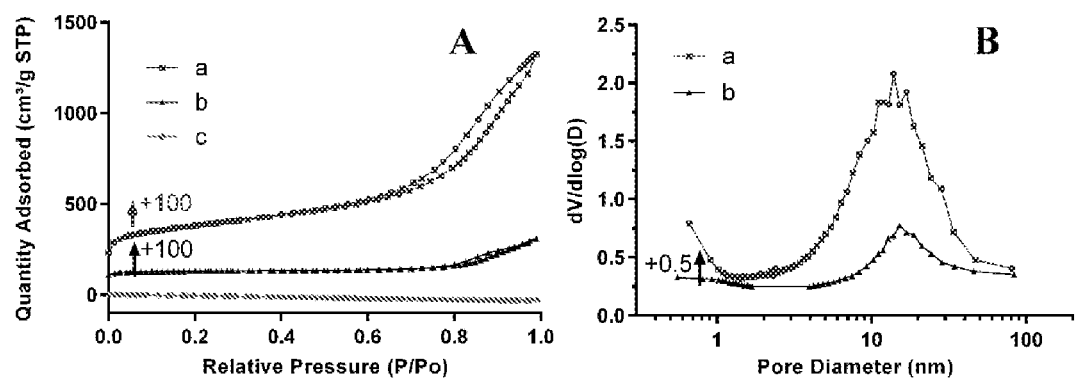
FIG. 5 shows $N_2$ sorption isotherm (A) and pore size distribution (B) of (a) Asymmetric carbon nanoparticles, (b) Asymmetric silica nanoparticles, (c) ABC heterotrimeric nanoparticles.

Example 2—a Bottom-Up Self Assembly of AV+BC Heterotrimeric Nanoparticles Vis a Facile One-Pot Approach As shown in FIG. 3a, the synthesis involves three molecular precursors: 3-aminophenol (AP), formaldehyde (F), tetraethyl orthosilicate (TEOS) in a basic solution containing ethylenediamine (EDA), ethanol, water and ammonia. The hydrolysis and condensation of TEOS firstly results in the formation of silica primary particles[51] and then Stober silica spheres[52] as a building block A. The polymerization of AP and F leads to APF oligomers, which further nucleate as a building block B preferentially on one side of A, leading to an AB heterodimeric structure with the sizes of both A and B blocks increasing with time. Afterwards, silica primary particles and APF oligomers co-condense, forming a building block C on the other side of A. Eventually an ABC type heterotrimeric nanoparticle with an acorn-like asymmetric morphology is constructed, which can be used to generate two different second-generation asymmetric nanoparticles (FIG. 3b): one asymmetric silica nanoparticle by calcination to remove APF polymer, another asymmetric carbon nanoparticle by carbonization in an inert atmosphere followed by selective silica etching. In addition, for the first time, we demonstrate that the nanoparticle cellular uptake is dependent on both nanoparticle symmetry and the phagocytic capacity of cells (FIG. 3c). Symmetry-polarized cellular take is preferred in cell lines with low phagocytic ability (e.g., KHOS and CHO-K1 cells), while asymmetry-polarized cellular uptake is advantageous in cell lines with high phagocytic ability (e.g., HCT116 and RAW264.7 cells).

Synthesis of the ABC Heterotrimeric Nanoparticles. Monodispersed ABC heterotrimeric nanoparticles was synthesized through a one-pot surfactant free process under alkaline condition in alcohol-water system. Typically, 3-aminophenol (0.41 g), formalin (37 wt %, 0.9 mL), and tetraethyl orthosilicate (TEOS, 1.75 mL) were added to the solution composed of ammonia aqueous solution (1.56 mL, 28 wt %), deionized water (10 mL), ethylenediamine (EDA, 0.175 mL) and ethanol (40 mL). The above solution was vigorously stirred at room temperature for 4 h. The as-synthesized particles were separated by centrifugation, and washed with ethanol and deionized water for three times. The final product was obtained by drying at 323 K overnight. The asymmetric silica nanoparticles were obtained by calcination of the pre-dried ABC heterotrimeric nanoparticles at 550° C. in air. Carbon product of the ABC heterotrimeric nanoparticles were achieved by calcining the sample under nitrogen atmosphere in a tube furnace at 700° C. with a heating rate of 3° C./min. Silica etching was carried out in an 8% HF aqueous solution.

Transmission electron microscope (TEM) images of the heterotrimeric nanoparticles (FIG. 3a, 3b) clearly showed an asymmetric nanostructure similar to the morphology of the fruit acorn, which is supported by the scanning electron microscopy (SEM) observations (FIG. 3c). The particles are monodispersed and uniform in size (~420 nm). From TEM images, the "bulge" (block B) has a hemispherical morphology with a smaller contrast than the "cap" (block C)(FIG. 3b). Moreover, the "cap" has a core with darker contrast and a shell with spike-like fine nanostructures.

Figure 2:
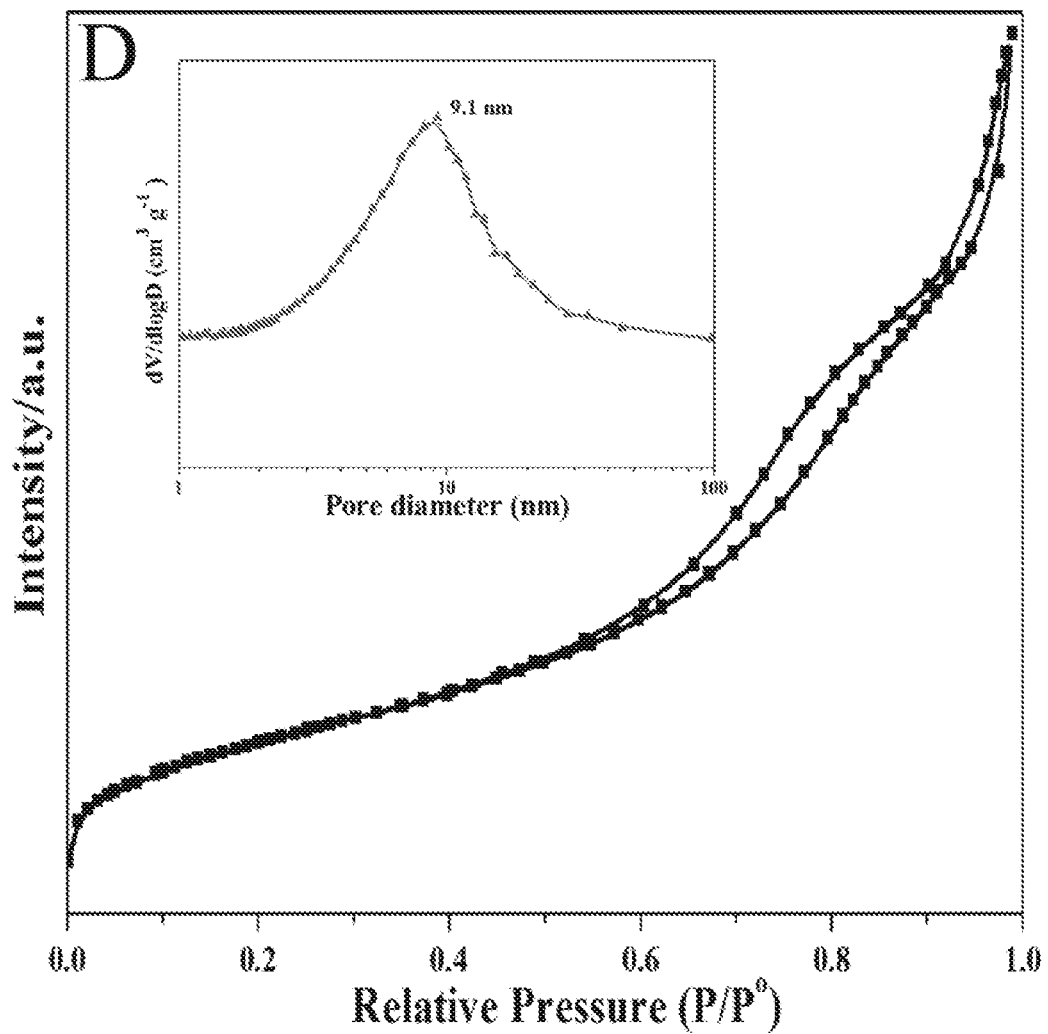
FIG. 2 shows $N_2$ adsorption/desorption isotherms and the corresponding pore size distributions (inset) of the monodisperse mesoporous silicon nanoparticles of example 1.

Scanning TEM (STEM) coupled with energy dispersive X-ray spectroscopy (EDS) elemental mapping (C, N, O, Si) was used to record the heterogeneous composition in the heterotrimeric nanoparticles (FIG. 3d-i). A STEM image (FIG. 3d) showed the same acorn-like morphology as FIG. 3a-c. The C (FIG. 3e) and N mapping (FIG. 3f) exhibited a higher intensity in the hemispherical "bulge" region, while the O (FIG. 3g) and Si (FIG. 3h) intensity was observed predominantly in the "cap" region. This heterogeneous distribution of C, N, O, Si elements was more evident in the overlapped image (FIG. 3i). The above results indicate that the acorn-like heterotrimeric nanoparticle has a structure as shown in FIG. 2: the "bulge" (block B) is composed of APF without $SiO_2$, while the "cap" has a silica-rich core (block A) and a silica-APF composite shell (block C).

After removing APF polymer from the ABC heterotrimeric nanoparticles by calcination, well dispersed asymmetric silica nanoparticles (composed of block A and part of block C) are obtained. From the high magnification TEM images (FIG. 3a), the measured particle size is around 370 nm. It is found that the asymmetric silica nanoparticle has a solid silica core (~230 nm in diameter). Noticeably, the silica core is densely coated by nano-sized silica spikes (~70 nm in length) which attached only on one side of the silica sphere, leaving the other side uncovered, confirmed by the related SEM image (FIG. 2b). From the TEM images of asymmetric carbon nanoparticles, a high contrast "bulge" with hemispherical morphology and a hollow mesoporous "cap" structure is observed in the particle (FIG. 1c). The hollow morphology and asymmetric structure can be clearly identified through the TEM images. The particle size of the obtained asymmetric carbon nanoparticles is around 380 nm. The diameter of the cavity is similar to the size of the silica core in FIG. 1a, which further confirm existence of the solid silica core inside the "cap" of ABC heterotrimeric nanoparticles Dynamic light scattering (DLS) measurement was carried out to analyse the dispersity and particle size of the ABC heterotrimeric nanoparticles, asymmetric silica nanoparticles and asymmetric carbon nanoparticles (Figure S1). DLS values show that all the three nanoparticles are monodispersed in water with a polydispersity index (PDI) less than 0.3. The measured hydrodynamic particle sizes of each nanoparticles are larger than their TEM results, which is caused by the hydration layer around silica nanoparticles.[53]

To characterize the porous structure of the synthesized asymmetric nanoparticles, $N_2$ sorption-desorption analysis was conducted. The results are presented in Figure S2. The nitrogen adsorption and desorption isotherm of asymmetric silica nanoparticles and asymmetric carbon nanoparticles show typical type IV isotherms as defined by IUPAC.[54] No porous structure can be observed for ABC heterotrimeric nanoparticles. Barrett-Joyner-Halenda (BJH) pore size distribution curve of asymmetric carbon nanoparticles in Figure S2 derived from adsorption branch exhibits a relatively broad peak centered at ~13.9 nm. While for asymmetric silica nanoparticles, the pore size distribution curve is centered at ~15.1 nm. Detailed textural parameters are listed in Table S1. The Brunauer-Emmett-Teller (BET) surface area and pore volume of asymmetric silica nanoparticles are 97.6 $m^2 \cdot g^{-1}$ and 0.33 $cm^3 \cdot g^{-1}$. For the asymmetric carbon nanoparticles, the BET surface area and pore volume are 954.3 $m^2 \cdot g^{-1}$ and 1.93 $cm^3 \cdot g^{-1}$, respectively.

Figure 6:
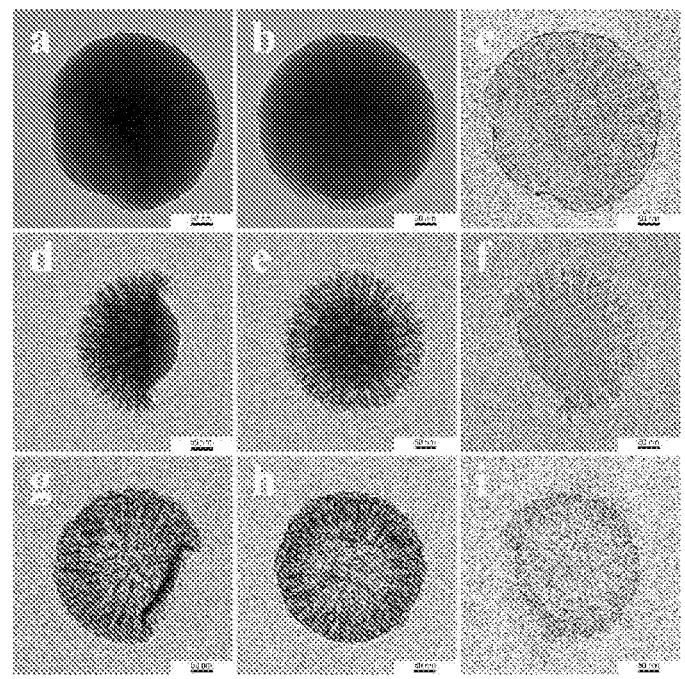
FIG. 6 shows tilting TEM images of (a, b) ABC heterotrimeric nanoparticle (from +120° to 0°), (d, e) asymmetric silica nanoparticle (from 0° to +90°) and (g, h) asymmetric carbon nanoparticle (from −55° to +55°). ET slides of (c) ABC heterotrimeric nanoparticle, (f) asymmetric silica nanoparticle, and (i) asymmetric carbon nanoparticle.

For the morphology characterization of three-dimensional (3D) nanoparticles, especially for asymmetric nanoparticles, the overlapping features of conventional TEM may complicate the analysis of those nanostructures and provide misleading information. This is because the images obtained by TEM are 2D projections of 3D objects.[55,40,41] In the case of ABC heterotrimeric nanoparticles, the "cap" is larger than the "bulge". When the electron beam passed from the "cap" to the "bulge", it will result in the appearance of symmetric spheres as shown in FIG. 3a (indicated by arrows).[56,57] Therefore, Electron tomography (ET) as a rapidly developing technique is applied for the morphology characterization of the ABC heterotrimeric nanoparticles and its second-generations. The related tilting TEM images are shown in FIG. 6. From FIG. 6a&b, one can see clearly the ABC heterotrimeric nanoparticle changing from an asymmetric structure to a spherical structure with a tilt axis ranging from +120° to 0°. As for asymmetric silica nanoparticles (FIG. 6d&e) and asymmetric carbon nanoparticles (FIG. 6g&h), asymmetric and symmetric structures can be clearly observed before (FIG. 6d&g) and after (FIG. 6e&h) tilting, respectively.

To study the detailed structures of the as prepared nanoparticles, ET slice cuts parallel to the symmetry axis from the center were generated by using IMOD software.[58] For the ABC heterotrimeric nanoparticle, ET slice (FIG. 6c) shows a three compartment structure, where the "bulge" and the "cap" can be easily seen. FIG. 6f presents that asymmetric silica nanoparticle has an obviously asymmetric morphology with only one side of the silica core coated by silica nano spikes. For asymmetric carbon nanoparticle, a hollow asymmetric structure was shown in FIG. 6i, the hollow void of which perfectly replicates the shape of the asymmetric silica nanoparticle as shown in FIG. 6f. This is consistent with the previous results.

Figure 7:
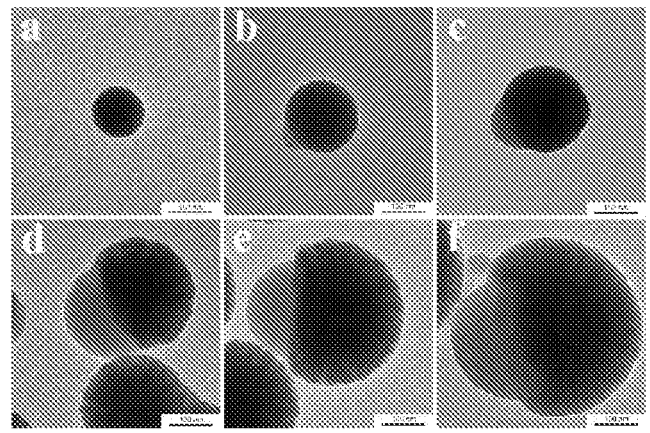
FIG. 7 shows TEM images of morphological evolution of the ABC heterotrimeric nanoparticle collected at different reaction time. (a) 5 min; (b) 10 min; (c) 15 min; (d) 30 min; (e) 1 h; (f) 3 h.
Figure 8:
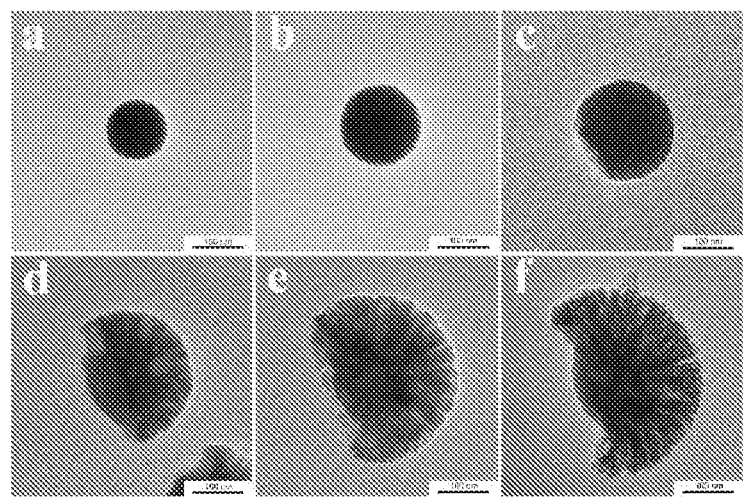
FIG. 8 shows TEM images of morphological evolution of the calcined sample of ABC heterotrimeric nanoparticles collected at different reaction time. (a) 5 min; (b) 10 min; (c) 15 min; (d) 30 min; (e) 1 h; (f) 3 h.
Figure 9:
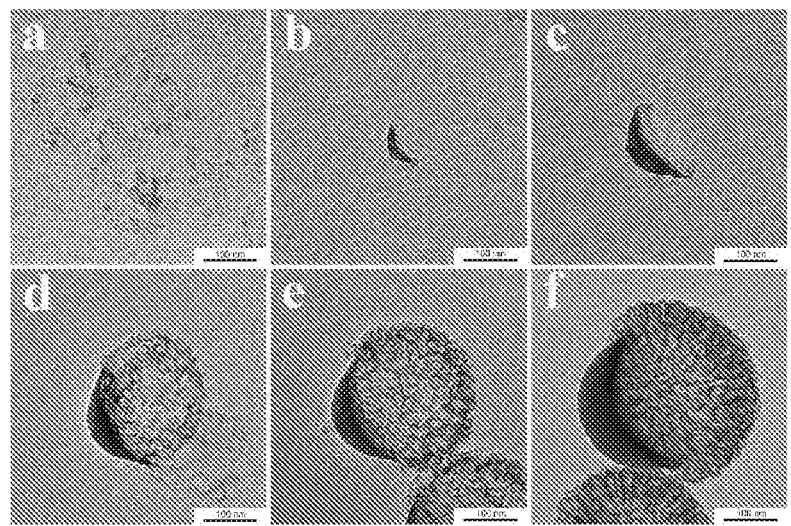
FIG. 9 shows TEM images of morphological evolution of the calcined sample of the carbon product of ABC heterotrimeric nanoparticles synthesized at different reaction time. (a) 5 min; (b) 10 min; (c) 15 min; (d) 30 min; (e) 1 h; (f) 3 h.

In order to investigate the formation mechanism of the ABC heterotrimeric nanoparticles, a time-dependent study was conducted. Samples were collected with different reaction time (5 min, 10 min 15 min, 30 min, 1 h and 2 h) during preparation. TEM images of the as-synthesized samples are shown in FIG. 7. TEM images of their related silica products and carbon products are shown in FIG. 8 and FIG. 9, respectively. Under the reaction condition, the hydrolysis and condensation of TEOS first form silica spheres (particle size ~100 nm) within 5 min (FIG. 7a and FIG. 8a) because TEOS reacts faster than the polymerization reaction of APF.[26,52] The relatively slower reaction kinetic rate of APF is revealed by FIG. 9a, since only disordered carbon structure can be found, which means 3-aminophenol and formaldehyde starts to form APF oligomers at ~5 min., After 10 min of reaction, a small dense APF polymer "bulge" (block B, low contrast) grows on the silica core (block A) forming a asymmetric AB heterodimeric structure, as the related calcined sample show only the existence of silica sphere (~160 nm) (FIG. 8b) and the related carbonized sample show the presence of a carbon "bulge" (FIG. 9b) which was coming from the "bulge" shagged APF polymer. The formation mechanism of the above asymmetric "head-tail" structure is similar to the classical island growth mode of Volmer-Weber.[59,60] By prolonging the reaction time to 15 min, the sizes of both blocks A and B increase with time (FIG. 7c, FIG. 8c and FIG. 9c) which is thermodynamically favored by the self-regulated homogeneous-heterogeneous nucleation mechanism.[12,61,62] After the formation of the AB heterodimeric structure, the third compartment (block C) starts to coat on block A at the reaction time of 30 min as shown in FIG. 7d It is interesting to notice that block B and block C both grow in size with the reaction going on (FIG. 7e&f) and the nanoparticles reached to a final size of ~420 nm.

During the experiment, we noticed that the amount of EDA introduced into the reaction system played a key role in determining the structure of the obtained nanoparticles Therefore, an interaction modulated sequential asymmetric deposition mechanism is proposed accordingly. When no EDA or low amount of EDA was added, only homogeneous nucleation of APF polymer spheres and silica spheres can be observed (FIG. 10a,b&c), which can be easily understood that, due to the negatively charged properties of APF oligomer[63] and in situ generated silica primary particles[64], the interaction between silica primary particles and APF oligomer was limited which led to the formation of isolated APF polymer spheres and silica spheres.

With a higher EDA amount of 0.175 mL, the positive charged EDA functions as a binder, which can react with both the preformed silica cores and APF oligomers. Therefore, the interaction between silica primary particles and APF oligomer was enhanced, which is beneficial for the cooperative assembly. Under the EDA amount of 0.175 mL, since the nucleation and growth process of silica and APF polymer can be triggered at different time point due to the fast hydrolysis and condensation rate of silica precursor.[65] Block A was quickly formed as a stable colloidal suspension in the reaction mixture. The size of block A kept growing and the condensation rate of silica primary particles decreased as a result of the consumption of the silica precursors. At the same time, the polymerization rate of 3-aminophenol and formaldehyde start to accelerate as shown by the indication of the existence of amorphous APF polymer in Fig. S4a. When Block A reached to a size of ~170 nm (FIG. 7b), the condensation rate of silica primary particles and the polymerization rate of APF became very close. Previous reports showed that if the polymerization rate of the two participant distinct a lot, only core-shell rather than asymmetric structures can be obtained.[66-68] Under the present of suitable amount of EDA and the similar polymerization rate of silica primary particles and APF oligomers, once the APF oligomer overcame the energy barrier for nucleation, under the heterogeneous nucleation mechanism,[12'74] APF oligomer favoured to nucleate on the silica cores heterogeneously to reduce the surface energy (the formation of particle AB, as shown in FIG. 1, and FIG. 7b).[69,70] As a result, the in situ generated silica cores is partially deposited by APF oligomers, which lead to the formation of the observable APF "bulge" domain in the final asymmetric ABC heterotrimeric nanoparticle.

At the time when block B asymmetric deposited on one side of block A, a large amount of silica precursor had been consumed to form block A, which means limited amount of silicate oligomers exist in the reaction solution. With the help of EDA, the existed silicate oligomers can react with phenolic resin to form some phenol-containing silicate oligomers species.[71,72] At this stage, APF oligomers and the phenol-containing silicate oligomers are predominant and coexist in the solution. For APF oligomers, it will continue to deposit on block B (C—O—C bond rich) since the same chemical composition. While for the phenol-containing silicate oligomers, it prefer to further condense on the silica domain part (block A, Si—O—Si bond rich). As a result of the competitive and cooperative assembly process between silica primary particles and APF oligomer, a "cap" (block C) can be found coating on the silica domain of AB heterodimeric nanoparticle forming the ABC heterotrimeric nanoparticles.

Figure 10:
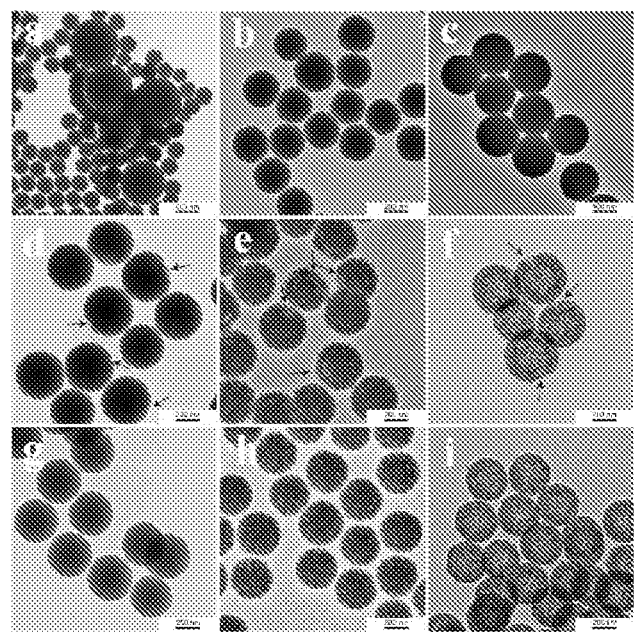
FIG. 10 shows TEM images of APF-silica nanoparticle with different amount of EDA. (a,b,c) 0 mL; (d,e,f) 0.200 mL; (g,h,i) 0.215 mL. As synthesized samples (a,d,g), calcined samples (b,e,h), carbonized and HF etched samples (c,f,i)

When further increase the EDA amount to 0.200 mL, more formalin was consumed by EDA to form Schiff base accordingly.[26,73] Therefore, less APF precursors was available for the formation of the APF "bulge" resulting in the decrease of the "bulge" domain (block B) of the ABC heterotrimeric nanoparticles, as pointed by the arrows in FIG. 10d,e&f. A further higher EDA amount (0.215 mL) consumes more formalin and favors the heterogeneous nucleation of APF polymer and silica forming symmetric APF/silica composite (FIG. 10g) with no APF "bulge" domain. By calcination, the APF/silica composite can be converted to symmetric silica nanoparticles (FIG. 10h) where the nano spikes-like silica subunit symmetrically coated on the silica core surface, and hollow mesoporous carbon spheres (FIG. 10i) can be obtained by the carbonization and HF etching of silica of the APF/silica composite. This demonstrate the symmetric morphology of the APF/silica composite synthesized at the higher EDA amount (0.215 mL).

Example 3

Figure 11:
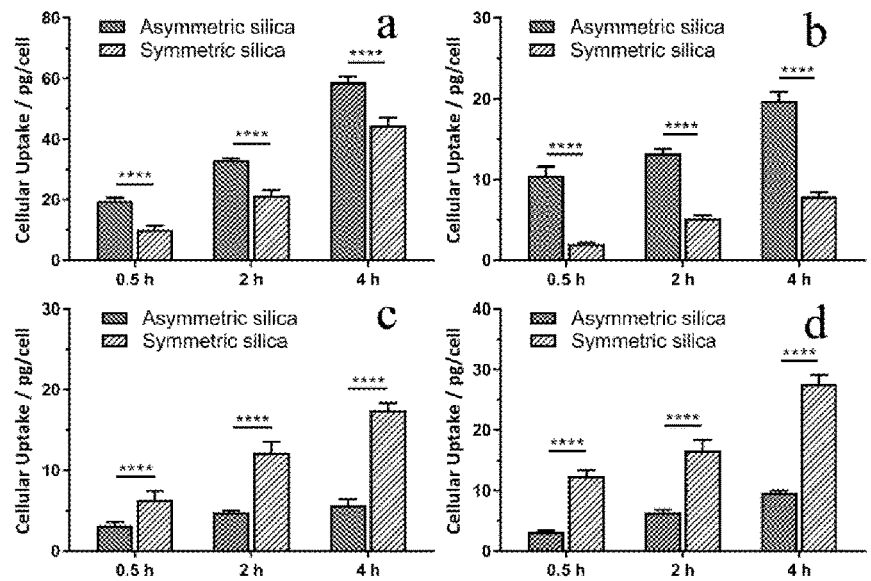
FIG. 11 shows time dependent cellular uptake of asymmetric silica and symmetric silica nanoparticles in four cell lines investigated by ICP-OES. RAW 264.7 cells (a); HCT116 cells (b); CHO-K1 cells (c); KHOS cells (d)

We further investigated the cellular uptake performance between the asymmetric silica nanoparticles and a symmetric silica nanoparticles (sample from FIG. 10h) in RAW 264.7 cells, HCT116 cells, CHO-K1 cells and KHOS cells. We quantified the cellular uptake amount of each silica nanoparticles by measuring the total amounts of silicon by ICP-OES. The cellular uptake results at different incubation time points (0.5 h, 2 h and 4 h) are shown as the amount of silicon per cell in FIG. 11. From the figure, it is obvious to see that, for cells with high phagocytic capacity (RAW 264.7 and HCT116 cells), the asymmetric silica nanoparticles show higher cellular uptake amount than the symmetric silica nanoparticles at each incubation time point. For instance, in macrophage RAW 264.7 cell line, ~20 pg of the asymmetric silica nanoparticles was uptaken by each cell after incubation at 37° C. for 0.5 h. while only ~10 pg of the symmetric silica nanoparticles per cell was uptaken after the same incubation time. With the increase of nanoparticle and cell incubation time, both the cellular uptake amount of the asymmetric silica nanoparticles and the symmetric silica nanoparticles increase. And the asymmetric silica nanoparticles still show higher uptake amount than the symmetric silica nanoparticles. This result means that for cell lines with relative high phagocytic capacity (RAW 264.7 and HCT116 cells), they preferentially uptake the asymmetric silica nanoparticle with asymmetric structure where the surface is asymmetrically coated by silica nano spikes rather than the symmetric silica nanoparticles with nano spikes symmetrically coating on the silica core surface.

However, it is noteworthy that the cellular uptake results for cell lines with low phagocytic capacity show completely opposite preference compared with the previous results. As shown in FIG. 6c, the symmetric silica nanoparticles were internalized into CHO-K1 cells with higher amount (~6 pg/cell) then the asymmetric silica nanoparticle (~3 pg/cell) at incubation time of 0.5 h, and the uptake amounts of the two type nanoparticles increased during the following hours. At the incubation time of 4 h, the symmetric silica nanoparticle uptake by CHO-K1 cells reach to ~17 pg/cell, which was much higher than that for the asymmetric silica nanoparticles (~5 pg/cell). Similar observations can be found in KHOS cell line.

Figure 12:
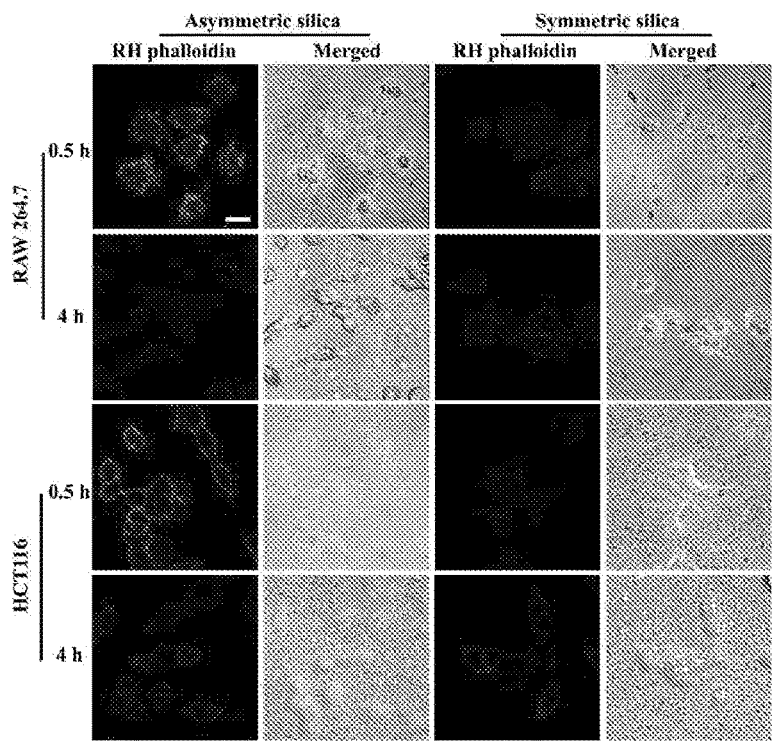
FIG. 12 shows fluorescent and merged images of RAW 264.7 and HCT116 cell lines, after the addition of the asymmetric silica and symmetric silica nanoparticles, being fixed at 0.5 or 4 hours and stained for polymerized actin with RH phalloidin. Scale bar, 20 µm.

After evaluating the cellular uptake performance of the asymmetric silica nanoparticles and the symmetric silica nanoparticles among RAW 264.7, HCT116 cells, CHO-K1 and KHOS cells lines by ICP-OES, we were interested if the phagocytic capacity of different cells might play a role in the uptake process of the nanoparticles. Previous report has shown that the shape of nanoparticles plays a dominant role in activate the phagocytosis pathway.[45] We investigated whether the distinct cellular uptake preferences of the two silica nanoparticles with different surface symmetry are resulted from the phagocytic capacity different among the four cell lines. To establish the role of the phagocytic capacity of a cell line on the nanoparticles' internalization, we conducted a confocal analysis. To observe the activation of the phagocytosis pathway, we use rhodamine phalloidin (RH phalloidin) to stain the actin filaments which is usually involved in the phagocytosis process.[74-76] The functionality of the phagocytosis pathway can be verified via the red fluorescence from the confocal images. FIG. 12 show the confocal microscopy images of RAW 264.7 and HCT116 cells incubated with asymmetric silica and symmetric silica nanoparticles at various incubation times (0.5 h, 2 h, 4 h), respectively. As shown in FIG. 12, from the internalization result of the cells with higher phagocytic capacity (RAW 264.7 and HCT116),[34,77,78,31,72,73] the phagocytosis pathway is activated at very early time point (0.5 h) as shown by the red fluorescence. For example, for the uptake of asymmetric silica nanoparticle, as shown in the confocal image result of RAW 264.7 cell line at 0.5 h. The cells presented a peripheral red fluorescent label that show clearly the spatial cell morphology. The short time course of particle uptake by macrophage phagocytosis pathway is consistent with previous report.[79] The limited red fluorescent can be observed at incubation time of 2 h and 4 h for RAW 264.7 cell line, which means the phagocytosis process is relative weak after the initial fast internalization stage. Similar results was found in the uptake of the asymmetric silica nanoparticle in HCT116 cell line (FIG. 12), which shows that the phagocytosis pathway of HCT116 cells can be easily activated by the asymmetric silica nanoparticles. However, for the cellular uptake of the symmetric silica nanoparticles in RAW264.7 and HCT116 cell lines, as judged by the red fluorescent intensity of the confocal images in FIG. 12, the phagocytic pathway of both RAW264.7 and HCT116 cell lines can be activated at short incubation time of the symmetric silica nanoparticles with the cells. However, the fluorescent intensity is less strong as compared with that of the asymmetric silica nanoparticles. The fast activation of phagocytosis pathway of RAW264.7 and HCT116 cells by the incubation of the asymmetric or symmetric nanoparticles further demonstrate the high phagocytic capacity of the two cell lines, which is consistent with previous reports.[40,81,82] And these two cell lines uptake more of the asymmetric silica nanoparticle over the symmetric silica nanoparticles.

Figure 13:
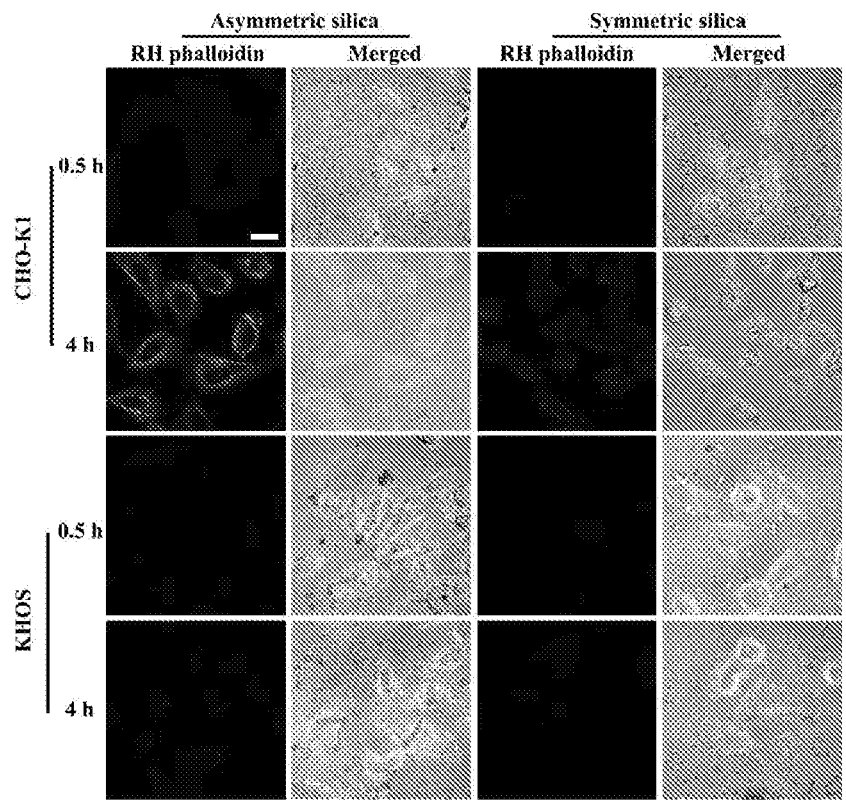
FIG. 13 shows fluorescent and merged images of CHO-K1 and KHOS cell lines, after the addition of the asymmetric silica and symmetric silica nanoparticles, being fixed at 0.5 or 4 hours and stained for polymerized actin with RH phalloidin. Scale bar, 20 µm.

FIG. 13 shows the actin filaments staining results of CHO-K1 and KHOS cells with different nanoparticle and cell incubation time (0.5 h, 2 h and 4 h). From the figure, the phagocytosis of two nanoparticles in CHO-K1 cells started after 4 h of incubation, which is much delayed compared with RAW 264.7 and HCT116 cell lines, suggesting the CHO-K1 cell can display relative low extend phagocytic activity.[80-82] While the phagocytosis pathway of KHOS cells was not activated during the experiment (up to 4 h), which is consistent with the negligible phagocytic capacity of KHOS cells. Our results provide direct comparison between asymmetric and symmetric nanoparticles with the phagocytic capacity of a cell line.

Figure 14:
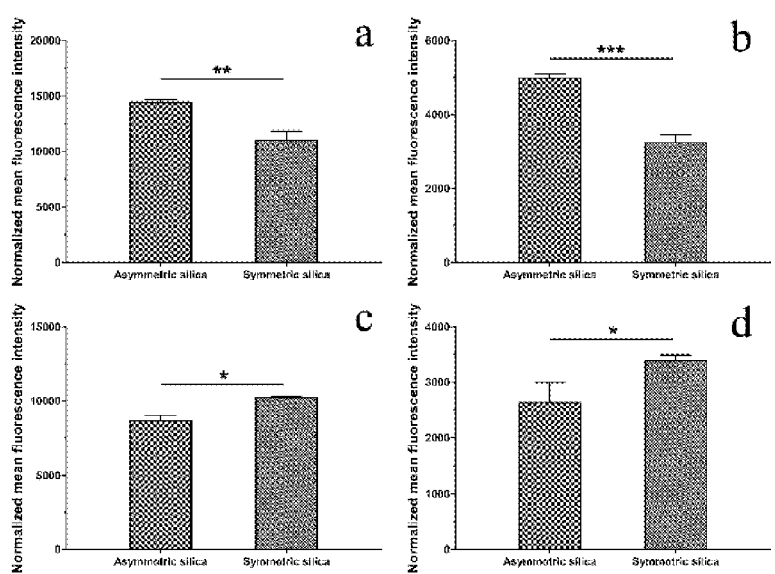
FIG. 14 shows cellular uptake of the asymmetric silica nanoparticle and the symmetric silica nanoparticle in RAW 264.7 cells (a); HCT116 cells (b); CHO-K1 cells (c); KHOS cells (d) cell lines as determined by Fluorescence-activated cell sorting (FACS) analysis.

To further evaluate the contribution of the actin polymerization based phagocytosis to the cellular uptake of each type of nanoparticles, we set out to investigate cellular uptake of the two silica nanoparticles by applying a phagocytosis pathway inhibitor cytochalasin D (denoted as Cyto D) which is widely used to disrupt actin polymerization.[83,84] Nanoparticles uptake by each cell line was measured at short incubation time (0.5 h) due to the reason that the blocking of one uptake pathway can activate other endocytic pathways.[85,86] In the control group, where no inhibitor was introduced, we compared the cellular uptake level of the symmetric silica and the asymmetric silica nanoparticles in each cell lines. Rhodamine-B-isothiocyanate (RITC) was conjugated to the silica nanoparticles, the normalized cell-associated mean fluorescence intensity was analysed by fluorescence-activated cell sorting (FACS) (FIG. 14). In the figure, the cellular uptake evaluated by FACS show a similar trend compared with the ICP result in FIG. 11. After the introduction of the pathway inhibitor Cyto D, the result is shown in FIG. 13. For cell lines with low phagocytic capacity (KHOS and CHO-K1 cell lines), the block of actin polymerization by Cyto D did not significantly influence the uptake result of nanoparticles regardless of the nanoparticle is symmetric or asymmetric. However, the nanoparticles internalization was reduced to some extend by Cyto D in HCT116 cells, especially for the asymmetric silica nanoparticle, which show significant difference compared to the control group. Moreover, with the increase of the phagocytic capacity of the cells, for RAW264.7 cells, 35% of inhibition can be observed for the asymmetric silica nanoparticles. This suggests that the phagocytosis pathway participated strongly in the endocytosis of the asymmetric silica nanoparticles. This result signifies that the phagocytic capacity of a cell line has significant influence on the cellular uptake preference between the asymmetric silica nanoparticles and the symmetric silica nanoparticles.

In the present specification and claims (if any), the word 'comprising' and its derivatives including 'comprises' and 'comprise' include each of the stated integers but does not exclude the inclusion of one or more further integers.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the appended claims (if any) appropriately interpreted by those skilled in the art.

CITATION LIST

1. Du, J.; O'Reilly, R. K. *Chemical Society reviews* 2011, 40, 2402.
2. Hu, J.; Zhou, S.; Sun, Y.; Fang, X.; Wu, L. *Chemical Society reviews* 2012, 41, 4356.
3. Hodges, J. M.; Schaak, R. E. *Accounts of Chemical Research* 2017.
4. Jiang, S.; Granick, S.; Schneider, H.-J. Janus particle synthesis, self-assembly and applications; *Royal Society of Chemistry*, 2012.
5. Wang, C.; Xu, C.; Zeng, H.; Sun, S. *Advanced materials* 2009, 21, 3045.
6. Lattuada, M.; Hatton, T. A. *Nano Today* 2011, 6, 286.
7. Feyen, M.; Weidenthaler, C.; Schüth, F.; Lu, A.-H. *Journal of the American Chemical Society* 2010, 132, 6791.
8. Jiang, S.; Schultz, M. J.; Chen, Q.; Moore, J. S.; Granick, S. *Langmuir: the ACS journal of surfaces and colloids* 2008, 24, 10073.
9. Lattuada, M.; Hatton, T. A. *Journal of the American Chemical Society* 2007, 129, 12878.
10. HoonáKim, S.; WonáNam, S.; WooaCheong, I. *Chemical communications* 2011, 47, 2634.
11. Casavola, M.; Buonsanti, R.; Caputo, G.; Cozzoli, P. D. *European Journal of Inorganic Chemistry* 2008, 2008, 837.
12. Carbone, L.; Cozzoli, P. D. *Nano Today* 2010, 5, 449.
13. Crane, C. C.; Tao, J.; Wang, F.; Zhu, Y.; Chen, J. *The Journal of Physical Chemistry C* 2014, 118, 28134.
14. Schick, I.; Lorenz, S.; Gehrig, D.; Schilmann, A.-M.; Bauer, H.; Panthofer, M.; Fischer, K.; Strand, D.; Laquai, F.; Tremel, W. *Journal of the American Chemical Society* 2014, 136, 2473.
15. Bradley, M. J.; Read, C. G.; Schaak, R. E. *The Journal of Physical Chemistry C* 2015, 119, 8952.
16. Hodges, J. M.; Morse, J. R.; Williams, M. E.; Schaak, R. E. *Journal of the American Chemical Society* 2015, 137, 15493.
17. Read, C. G.; Gordon, T. R.; Hodges, J. M.; Schaak, R. E. *Journal of the American Chemical Society* 2015, 137, 12514.
18. Amirav, L.; Alivisatos, A. P. *The Journal of Physical Chemistry Letters* 2010, 1, 1051.
19. Khon, E.; Lambright, K.; Khnayzer, R. S.; Moroz, P.; Perera, D.; Butaeva, E.; Lambright, S.; Castellano, F. N.; Zamkov, M. *Nano letters* 2013, 13, 2016.
20. Buck, M. R.; Schaak, R. E. *Angewandte Chemie International Edition* 2013, 52, 6154.
21. Scarfiello, R.; Nobile, C.; Cozzoli, P. D. *Frontiers in Materials* 2016, 3, 56.
22. Reculusa, S.; Poncet-Legrand, C.; Perro, A.; Duguet, E.; Bourgeat-Lami, E.; Mingotaud, C.; Ravaine, S. *Chemistry of Materials* 2005, 17, 3338.
23. Qu, L.; Hu, H.; Yu, J.; Yu, X.; Liu, J.; Xu, Y.; Zhang, Q. *Langmuir: the ACS journal of surfaces and colloids* 2017.
24. Tran, N.; Mulet, X.; Hawley, A. M.; Conn, C. E.; Zhai, J.; Waddington, L. J.; Drummond, C. J. *Nano letters* 2015, 15, 4229.
25. Zhao, J.; Niu, W.; Zhang, L.; Cai, H.; Han, M.; Yuan, Y.; Majeed, S.; Anjum, S.; Xu, G. *Macromolecules* 2012, 46, 140.
26. Liu, Y.; Zhang, H.; Noonan, O.; Xu, C.; Niu, Y.; Yang, Y.; Zhou, L.; Huang, X.; Yu, C. *Chemistry—A European Journal* 2016, 22, 14962.
27. Li, Z.; Barnes, J. C.; Bosoy, A.; Stoddart, J. F.; Zink, J. I. *Chemical Society reviews* 2012, 41, 2590.
28. Peer, D.; Karp, J. M.; Hong, S.; Farokhzad, O. C.; Margalit, R.; Langer, R. *Nature nanotechnology* 2007, 2, 751.
29. Stark, W. J. *Angewandte Chemie International Edition* 2011, 50, 1242.
30. Mao, Z.; Zhou, X.; Gao, C. *Biomaterials science* 2013, 1, 896.
31. Oh, N.; Park, J.-H. *International journal of nanomedicine* 2014, 9, 51.
32. Kettler, K.; Veltman, K.; van de Meent, D.; van Wezel, A.; Hendriks, A. J. *Environmental toxicology and chemistry* 2014, 33, 481.
33. Conner, S. D.; Schmid, S. L. *Nature* 2003, 422, 37.
34. Aderem, A.; Underhill, D. M. *Annual review of immunology* 1999, 17, 593.
35. Rabinovitch, M. *Trends in cell biology* 1995, 5, 85.
36. Gagnon, E.; Duclos, S.; Rondeau, C.; Chevet, E.; Cameron, P. H.; Steele-Mortimer, O.; Paiement, J.; Bergeron, J. J.; Desjardins, M. *Cell* 2002, 110,119.
37. Kucharzik, T.; Lugering, N.; Rautenberg, K.; Liigering, A.; Schmidt, M.; Stoll, R.; Domschke, W. *Annals of the New York Academy of Sciences* 2000, 915, 171.
38. Lee, C. S.; Penberthy, K. K.; Wheeler, K. M.; Juncadella, I. J.; Vandenabeele, P.; Lysiak, J. J.; Ravichandran, K. S. *Immunity* 2016, 44, 807.
39. Neutra, M. R.; Frey, A.; Kraehenbuhl, J.-P. *Cell* 1996, 86, 345.
40. Dasgupta, S.; Auth, T.; Gompper, G. *Nano letters* 2014, 14, 687.
41. Mitragotri, S.; Lahann, J. *Nature materials* 2009, 8, 15.
42. Best, J. P.; Yan, Y.; Caruso, F. *Advanced healthcare materials* 2012, 1, 35.
43. Chithrani, B. D.; Ghazani, A. A.; Chan, W. C. *Nano letters* 2006, 6, 662.
44. Chithrani, B. D.; Chan, W. C. *Nano letters* 2007, 7, 1542.
45. Champion, J. A.; Mitragotri, S. *Proceedings of the National Academy of Sciences of the United States of America* 2006, 103, 4930.
46. Möller, J.; Luehmann, T.; Hall, H.; Vogel, V. *Nano letters* 2012, 12, 2901.
47. Herd, H.; Daum, N.; Jones, A. T.; Huwer, H.; Ghandehari, H.; Lehr, C.-M. *ACS nano* 2013, 7, 1961.
48. Blechinger, J.; Bauer, A. T.; Torrano, A. A.; Gorzelanny, C.; Brauchle, C.; Schneider, S. W. *Small* 2013, 9, 3970.

49. Wang, W.; Wang, P.; Tang, X.; Elzatahry, A. A.; Wang, S.; Al-Dahyan, D.; Zhao, M.; Yao, C.; Hung, C.-T.; Zhu, X. *ACS central science* 2017, 3, 839.
50. Song, H.; Ahmad Nor, Y.; Yu, M.; Yang, Y.; Zhang, J.; Zhang, H.; Xu, C.; Mitter, N.; Yu, C. *Journal of the American Chemical Society* 2016, 138, 6455.
51. Carcouet, C. C.; van de Put, M. W.; Mezari, B.; Magusin, P. C.; Laven, J.; Bomans, P. H.; Friedrich, H.; Esteves, A. C. C.; Sommerdijk, N. A.; van Benthem, R. A. *Nano letters* 2014, 14, 1433.
52. Bogush, G.; Zukoski, C. *Journal of colloid and interface science* 1991, 142, 1.
53. Tolnai, G.; Csempesz, F.; Kabai-Faix, M.; Kalman, E.; Keresztes, Z.; Kovacs, A.; Ramsden, J.; Horvolgyi, Z. *Langmuir: the ACS journal of surfaces and colloids* 2001,17, 2683.
54. Sing, K. S. *Pure and applied chemistry* 1985, 57, 603.
55. Lobling, T. I.; Haataja, J. S.; Synatschke, C. V.; Schacher, F. H.; Müller, M.; Hanisch, A.; Groschel, A. H.; Müller, A. H. *ACS nano* 2014, 8, 11330.
56. Friedrich, H.; de Jongh, P. E.; Verkleij, A. J.; de Jong, K. P. *Chemical reviews* 2009, 109, 1613.
57. Zhang, H.; Yu, M.; Song, H.; Noonan, O.; Zhang, J.; Yang, Y.; Zhou, L.; Yu, C. *Chem. Mater* 2015, 27, 6297.
58. Kremer, J. R.; Mastronarde, D. N.; McIntosh, J. R. *Journal of structural biology* 1996, 116, 71.
59. Peng, Z.; Yang, H. *Nano Today* 2009, 4, 143.
60. Goebl, J. A.; Black, R. W.; Puthussery, J.; Giblin, J.; Kosel, T. H.; Kuno, M. *Journal of the American Chemical Society* 2008, 130, 14822.
61. Costi, R.; Saunders, A. E.; Banin, U. *Angewandte Chemie International Edition* 2010, 49, 4878.
62. Saunders, A. E.; Popov, I.; Banin, U. *Zeitschrift für anorganische and allgemeine Chemie* 2007, 633, 2414.
63. Arif, A. F.; Kobayashi, Y.; Balgis, R.; Ogi, T.; Iwasaki, H.; Okuyama, K. *Carbon* 2016, 107, 11.
64. Kobayashi, M.; Skarba, M.; Galletto, P.; Cakara, D.; Borkovec, M. *Journal of colloid and interface science* 2005, 292, 139.
65. Erdemir, D.; Lee, A. Y.; Myerson, A. S. *Accounts of chemical research* 2009, 42, 621.
66. Qu, L.; Hu, H.; Yu, J.; Yu, X.; Liu, J.; Xu, Y.; Zhang, Q. *Langmuir: the ACS journal of surfaces and colloids* 2017, 33, 5269.
67. Fuertes, A. B.; Valle-Vigon, P.; Sevilla, M. *Chemical communications* 2012, 48, 6124.
68. Yang, P.; Xu, Y.; Chen, L.; Wang, X.; Mao, B.; Xie, Z.; Wang, S.-D.; Bao, F.; Zhang, Q. *Nano letters* 2015, 15, 8397.
69. Wang, J.; Tsung, C.-K.; Hong, W.; Wu, Y.; Tang, J.; Stucky, G. D. *Chemistry of materials* 2004, 16, 5169.
70. Zhang, L.; Zhang, F.; Dong, W.-F.; Song, J.-F.; Huo, Q.-S.; Sun, H.-B. *Chemical communications* 2011, 47, 1225.
71. Song, J.-C.; Xue, F.-F.; Zhang, X.-X.; Lu, Z.-Y.; Sun, Z.-Y. *Chemical communications* 2017, 53, 3761.
72. Liu, R.; Shi, Y.; Wan, Y.; Meng, Y.; Zhang, F.; Gu, D.; Chen, Z.; Tu, B.; Zhao, D. *Journal of the American Chemical Society* 2006, 128, 11652.
73. Rivera, A.; Rios-Motta, J. *Tetrahedron letters* 2005, 46, 5001.
74. Welch, M. D.; Mullins, R. D. *Annual review of cell and developmental biology* 2002, 18, 247.
75. Dramsi, S.; Cossart, P. *Annual review of cell and developmental biology* 1998, 14, 137.
76. Allen, L.-A. H.; Aderem, A. *Current opinion in immunology* 1996, 8, 36.
77. Savill, J.; Wyllie, A.; Henson, J.; Walport, M.; Henson, P.; Haslett, C. *The Journal of clinical investigation* 1989, 83, 865.
78. Sanjuan, M. A.; Dillon, C. P.; Tait, S. W.; Moshiach, S.; Dorsey, F.; Connell, S.; Komatsu, M.; Tanaka, K.; Cleveland, J. L.; Withoff, S. *Nature* 2007, 450, 1253.
79. Geiser, M. *Journal of aerosol medicine and pulmonary drug delivery* 2010, 23, 207.
80. Bozue, J.; Moody, K. L.; Cote, C. K.; Stiles, B. G.; Friedlander, A. M.; Welkos, S. L.; Hale, M. L. *Infection and immunity* 2007, 75, 4498.
81. Frampton, A. R.; Stolz, D. B.; Uchida, H.; Goins, W. F.; Cohen, J. B.; Glorioso, J. C. *Journal of virology* 2007, 81, 10879.
82. Martin, C.; Etxaniz, A.; Uribe, K. B.; Etxebarria, A.; Gonzalez-Bullon, D.; Arlucea, J.; F. M.; Arechaga, J.; Ostolaza, H. *Scientific reports* 2015, 5, 13774.
83. Huang, J.-L.; Jiang, G.; Song, Q.-X.; Gu, X.; Hu, M.; Wang, X.-L.; Song, H.-H.; Chen, L.-P.; Lin, Y.-Y.; Jiang, D. *Nature communications* 2017, 8, 15144.
84. Metavarayuth, K.; Sitasuwan, P.; Zhao, X.; Lin, Y.; Wang, Q. *ACS Biomaterials Science & Engineering* 2016, 2, 142.
85. Ivanov, A. I. In *Exocytosis and Endocytosis*; Springer: 2008, p 15.
86. Dos Santos, T.; Varela, J.; Lynch, I.; Salvati, A.; Dawson, K. A. *PloS one* 2011, 6, e24438.

The invention claimed is:

1. A method of forming dendritic mesoporous silica nanoparticles comprising preparing a mixture containing one or more polymer precursors, a silica precursor, and a compound that reacts with silica and reacts with a polymer or oligomer formed from the one or more polymer precursors, wherein:
   the one or more polymer precursors comprise 3-aminophenol and -formaldehyde; and
   the silica precursor is selected from the group consisting of tetraethyl orthosilicate (TEOS), tetrapropyl orthosilicate (TPOS) tetrabutoxysilane (TBOS) and tetramethyl orthosilicate (TMOS); and
   the compound that reacts with silica and reacts with the polymer or oligomer formed from the one or more polymer precursors comprises ethylene diamine (EDA); wherein a mass ratio of EDA to (3-aminophenol and formaldehyde) falls within a range of from 0.20 to 0.28 in order to form asymmetric particles, and
stirring the mixture whereby nanoparticles are formed, wherein the silica precursor reacts to the compound more quickly than the one or more polymer precursors such that flail primary silica particles are initially formed, followed by formation of further silica and polymer or oligomer that are laid down on the primary silica particles to form particles that comprise the primary silica particles having extra silica and polymer or oligomer growing from the surface thereof, and subsequently treating the nanoparticles to remove polymer therefrom to form the dendritic mesoporous silica nanoparticles having outgrowths of silica spikes on the primary silica particle.

2. The method as claimed in claim 1 wherein the mixture further comprises an alcohol and water.

3. The method as claimed in claim 1 wherein the mixture is stirred at an alkaline or basic pH.

4. The method as claimed in claim 3 wherein the alkaline or basic pH is in a range of from about 8 to about 11.

5. The method as claimed in claim 1 wherein the mass ratio of EDA to (3-aminophenol and formaldehyde) falls within a range of from 0.23 to 0.27, in order to form asymmetric particles.

6. The method as claimed in claim 1 wherein the particles are removed or separated from a liquid phase, washed and dried and then treated to form the dendritic mesoporous silica nanoparticles.

7. The method as claimed in claim 1 wherein the particles are calcined in air or an oxygen containing atmosphere to thereby burn out the polymer or the oligomer, leaving behind the dendritic mesoporous silica nanoparticles.

8. The method as claimed in claim 7 wherein calcination is carried out at a temperature of from 500° to 1000° C., or from 500° to 700° C.

9. The method as claimed in claim 1 wherein the asymmetric nanoparticles are formed and the particles have a maximum particle size of up to 1000 nm, or up to 900 nm, or up to 800 nm.

10. A method of forming dendritic mesoporous silica nanoparticles comprising preparing a mixture containing one or more polymer precursors, a silica precursor, and a compound that reacts with silica and reacts with a polymer or oligomer formed from the one or more polymer precursors, wherein:
   the one or more polymer precursors comprise 3-aminophenol and formaldehyde; and
   the silica precursor comprises tetraethyl orthosilicate (TEOS); and
   the compound that reacts with silica and reacts with the polymer or oligomer formed from the one or more polymer precursors comprises ethylene diamine (EDA); wherein a molar ratio of EDA to TEOS falls within a range of from 0.20 to 0.46, in order to form asymmetric particles, and
stirring the mixture whereby nanoparticles are formed, wherein the silica precursor reacts to the compound more quickly than the one or more polymer precursors such that primary silica particles are initially formed, followed by formation of further silica and polymer or oligomer that are laid down on the primary silica particles to form particles that comprise the primary silica particles having extra silica and polymer or oligomer growing from the surface thereof, and subsequently treating the nanoparticles to remove polymer therefrom to form the dendritic mesoporous silica nanoparticles having outgrowths of silica spikes on the primary silica particle.

11. The method as claimed in claim 10 wherein the asymmetric nanoparticles are formed and the particles have a maximum particle size of up to 1000 nm, or up to 900 nm, or up to 800 nm.

12. The method as claimed in claim 10 wherein the mixture further comprises an alcohol and water.

13. The method as claimed in claim 10 wherein the mixture is stirred at an alkaline or basic pH.

14. The method as claimed in claim 13 wherein the alkaline or basic pH is in a range of from about 8 to about 11.

15. The method as claimed in claim 10 wherein the particles are removed or separated from a liquid phase, washed and dried and then treated to form the dendritic mesoporous silica nanoparticles.

16. The method as claimed in claim 10 wherein the particles are calcined in air or an oxygen containing atmosphere to thereby burn out the polymer or the oligomer, leaving behind the dendritic mesoporous silica nanoparticles.

17. The method as claimed in claim 16 wherein calcination is carried out at a temperature of from 500° to 1000° C., or from 500° to 700° C.

* * * * *